(12) United States Patent
Benosman et al.

(10) Patent No.: US 10,559,247 B2
(45) Date of Patent: Feb. 11, 2020

(54) DISPLAY CONTROL METHOD AND DEVICE FOR IMPLEMENTING SAID METHOD

(71) Applicants: CENTRE NATIONAL DE LA RECHERCHE SCIENTIFIQUE—CNRS, Paris (FR); UNIVERSITE PIERRE ET MARIE CURIE (PARIS 6), Paris (FR)

(72) Inventors: Ryad Benosman, Pantin (FR); Guillaume Chenegros, Trappes (FR); Sihem Kime, Paris (FR); Siohoi Ieng, Montreuil (FR); Jose-Alain Sahel, Paris (FR)

(73) Assignees: CENTRE NATIONAL DE LA RECHERCHE SCIENTIFIQUE—CNRS, Paris (FR); SORBONNE UNIVERSITE, Paris (FR)

( * ) Notice: Subject to any disclaimer, the term of this patent is extended or adjusted under 35 U.S.C. 154(b) by 330 days.

(21) Appl. No.: 15/129,055

(22) PCT Filed: Mar. 18, 2015

(86) PCT No.: PCT/FR2015/050654
§ 371 (c)(1),
(2) Date: Sep. 26, 2016

(87) PCT Pub. No.: WO2015/145025
PCT Pub. Date: Oct. 1, 2015

(65) Prior Publication Data
US 2017/0110045 A1    Apr. 20, 2017

(30) Foreign Application Priority Data

Mar. 26, 2014 (FR) .................................. 14 52557

(51) Int. Cl.
*G09G 3/20* (2006.01)
*A61N 1/05* (2006.01)
(Continued)

(52) U.S. Cl.
CPC ......... *G09G 3/2007* (2013.01); *A61N 1/0543* (2013.01); *G09G 3/2018* (2013.01);
(Continued)

(58) Field of Classification Search
CPC .. G09G 3/2007; G09G 3/2018; G09G 3/2085; G09G 3/346; G09G 3/2096;
(Continued)

(56) References Cited

U.S. PATENT DOCUMENTS

2008/0135731 A1    6/2008 Lichtsteiner et al.

FOREIGN PATENT DOCUMENTS

WO    2006/128315 A1    12/2006

OTHER PUBLICATIONS

International Search Report, dated May 28, 2015, from corresponding PCT application.
(Continued)

*Primary Examiner* — Abhishek Sarma
(74) *Attorney, Agent, or Firm* — Young & Thompson (57) ABSTRACT

A method of controlling the display of images in the form of a pixel array, includes for a pixel of the array, asynchronous information representing events concerning the pixel is received, a first activation of the pixel is actuated at an activation time determined by a first event of the asynchronous information, and at least a second activation of the pixel is actuated in order to repeat the first activation of the pixel at respective times defined by a refresh sequence.

16 Claims, 6 Drawing Sheets

(51) Int. Cl.
*A61F 2/14* (2006.01)
*G09G 3/34* (2006.01)

(52) U.S. Cl.
CPC ......... *G09G 3/2085* (2013.01); *G09G 3/2096* (2013.01); *G09G 3/346* (2013.01); *A61F 2/14* (2013.01); *G09G 2320/0252* (2013.01); *G09G 2360/144* (2013.01); *G09G 2370/00* (2013.01); *G09G 2380/08* (2013.01)

(58) Field of Classification Search
CPC ......... G09G 2360/144; G09G 2380/08; G09G 2370/00; G09G 2320/0252; A61F 1/0543; A61F 2/14
See application file for complete search history.

(56) References Cited

OTHER PUBLICATIONS

"Digital and Mixed Signal Oscilloscopes MSO/DP070000 Series Datasheet", Apr. 10, 2013, retrieved from the internet: URL:http://www.tek.com/sites/tek.com/files/media/media/resources/MSO-DP070000-Oscilloscope-Datasheet-23.pdf.

Kwabena A. Boahen, "Point-to-Point Connectivity Between Neuromorphic Chips Using Address Events", IEEE Transactions on Circuits and Systems II: Analog and Digitalsignal Processing, May 1, 2000, pp. 416-434, vol. 47, No. 5.

Stephen R. Deiss et al., "A Pulse Coded Communications Infrastructure for Neuromorphic Systems", Dec. 31, 1999, pp. 157-178, vol. 6.

Patrick Lichtsteiner et al., "A 128×128 120 dB 15 μs Latency Asynchronous Temporal Contrast Vision Sensor", IEEE Journal of Solid-State Circuits, Feb. 2008, pp. 566-576, vol. 43, No. 2.

Christoph Posch et al., "A QVGA 143 dB Dynamic Range Frame-Free PWM Image Sensor With Lossless Pixel-Leve Video Compression and Time-Domain CDS", IEEE Journal of Solid-State Circuits, pp. 259-275, Jan. 2011, vol. 46—No. 1.

Christoph Posch et al., "An Asynchronous Time-based Image Sensor", IEEE, 2008, pp. 2130-2133.

Office Action in European Patent Application No. 15 714 874.3 dated Jan. 30, 2019 with partial English machine translation provided.

Ni, "Asynchronous Event Based Vision: Algorithms and Applications to Microrobotics," Universite Pierre et Marie Curie, Paris VI, 2013, PHD Thesis.

Posch et al., "A Microbolometer Asynchronous Dynamic Vision Sensor for LWIR," IEEE Sensors Journal, vol. 9, No. 6, Jun. 2009, pp. 654-664.

FIG. 7 ial resolution providing maximum visual comfort.
DISPLAY CONTROL METHOD AND DEVICE FOR IMPLEMENTING SAID METHOD The present invention relates to methods for controlling the display of visual information based on asynchronous information, and to devices for implementing these control methods.

BACKGROUND OF THE INVENTION

Conventional methods for controlling display devices comprising a screen whereon the information is to be projected generally envisage a synchronous operating mode wherein the display of images in the form of a pixel array is performed substantially periodically. The display period determines the dynamic display range of the device, and is most often the result of a compromise between the hardware limitations of the devices (including those relating to the computing capabilities thereof), and the need to attain a temporal resolution providing maximum visual comfort.

This display period further corresponds to the period at which the display of the pixels of the array is refreshed, given that the display is controlled so as to display all the pixels of the array simultaneously or quasi-simultaneously. For example, the display of a video frame will be performed in certain systems by periodically displaying a sequence of sub-frames (so-called "even" sub-frames, corresponding to a subarray comprising the rows of even sequential number of the pixel array corresponding to the frame, and so-called "odd" sub-frames, corresponding to a subarray comprising the rows of odd sequential number of the pixel array corresponding to the frame), such that the set of pixels of each sub-frame will be displayed (or lit) periodically, the sub-frames being displayed in alternation at a frequency twice as high as the display frequency of the frames.

The temporal resolution that can be attained notably for systems intended for the general public is thus limited in that the display methods used envisage a quasi-simultaneous display of a large number of pixels of the corresponding pixel array, on the display screen, at a frequency in turn limited by the processing capabilities of these systems.

Moreover, it would appear that it is quasi-impossible to transpose conventional display methods in the context of the control of vision aid devices. Indeed, implants or optogenetic treatment methods require luminous stimulation signals of much higher intensity than that of ambient light. A vision aid implant placed under the eye, typically comprising an electrode around which one to three photodiodes are arranged, will only function effectively if these photodiodes receive light seven times more powerful than that of ambient light, such that the photodiodes can emit a stimulus. Similarly, current optogenetic treatments are only fully effective if the treated eye receives luminous signals having a specific wavelength and a luminous intensity ranging from two to seven times that of ambient light. The luminous powers required are thus so high that the use of conventional display methods, at these power levels, would cause lesions on users' visual organs.

As such, there is a need for display methods, not having the drawbacks of the conventional methods described above. In particular, a first need is that of providing display control methods suitable for attaining higher display resolutions than those resulting from the compromises made with conventional systems. A further need is that of providing display control methods which can be used for applications in the vision aid field.

SUMMARY OF THE INVENTION

The invention proposes a method for controlling the display of images in the form of a pixel array, comprising, for a pixel of the array: receiving the asynchronous information representing events concerning the pixel, actuating a first activation of the pixel at an activation time determined by a first event of the asynchronous information, and actuating at least a second activation of the pixel in order to repeat the first activation of the pixel at respective times defined by a refresh sequence.

The events relating to the pixel may according to the embodiment correspond to light variations concerning the pixel, the detection of a shape of interest or the detection of a primitive, and more generally to any type of asynchronous information concerning the pixel.

Methods for the acquisition or synthesis of a sequence of images by frames have the drawback of producing highly redundant data due to sampling over time according to a predefined frame clock frequency. Each frame represents a large number of pixels of an image if not a whole image, and includes information relating to pixels for which the information does not change from one frame to another, which generates redundancies in the data representing the image sequence. This redundancy can only be partially removed by compression encoding of a conventional video signal. Conversely, the use for each pixel of "event-based" asynchronous information makes it possible to obtain a very compact representation of an image sequence, due to the fact that the asynchronous information represents events. As such, when the events in question correspond for example to light variations concerning the pixel, the lack of light variations concerning a pixel is conveyed by the lack of event concerning this pixel, which thus does not generate redundant information concerning this pixel in the representation of the image sequence.

The activation of a pixel based on asynchronous information may be performed by observing—within a temporal resolution—the asynchronous nature of the event sequence for this pixel, so as carry out an activation of the pixel which is "event-driven".

In one example of an embodiment of the proposed method, the first activation command of the pixel is repeated according to the refresh sequence until the determination of the next activation time of the pixel by the events of the asynchronous information.

In one embodiment of the proposed method, the reception of the asynchronous information comprises the reception of a signal carrying the asynchronous information, and the first activation command of the pixel comprises the detection in the signal of a first item of information representing the first event and the activation command on detection of the first item of information representing the first event.

Furthermore, the refresh sequence may define activation times of the pixel separated by a time interval. This time interval between an event-driven activation and a refresh activation, or between two refresh activations, may for example be determined according to the retinal persistence of the human eye. The retinal persistence of the human eye constitutes a limit threshold which it is preferable not to exceed to perform a refresh display of the pixel, at the risk of degrading the visual comfort of the user. For example, this time interval will be chosen between 40 ms and 800 ms, and preferably between 40 ms and 150 ms, in order to prevent flicker effects, in the knowledge that a longer time interval corresponds to a lower refresh frequency and a decrease in the flow of display commands and associated computations.

In one embodiment of the proposed method, the activation commands are delivered in the form of electric stimulations applied to a visual prosthesis of a vision aid device.

The small quantity of data representing a sequence of images of an AER type asynchronous signal makes it possible to increase the intensity of the luminous excitation signals of the photoreceptors of a visual prosthesis or a visual organ to which an optogenetic treatment has been applied. Indeed, the proposed method makes it possible to only consider the display of a pixel when an event corresponding to this pixel is detected in the input data representing for example an image sequence, and only performing refresh displays at a much lower frequency than that of conventional display methods.

In a further particular embodiment, the activation commands are configured to control the display of pixels on a display screen of a device.

As such, the proposed method may be used for the generation of pixel activation commands, with a view to the display of an image sequence on the screen of any device, such as for example a television, smartphone, digital tablet, computer, monitor, GPS screen, etc.

The proposed method is also applicable to any display system by projection, for example onto a screen, whether physical or virtual.

In one embodiment of the proposed method, the activation refresh is performed for a plurality of pixels of the pixel array.

It is further possible to combine the event-driven display of a pixel which reproduces the asynchronous nature derived for example from an asynchronous signal received for display with a synchronous, i.e. periodic, refresh display, which may envisage a refresh display of all or part of the pixel array.

It is preferable in this embodiment with synchronous refresh display to choose a much lower refresh frequency than that of the current systems, in order to make best use of the asynchronism of event-driven displays for each pixel.

In one embodiment of the proposed method, the asynchronous signal comprises a train of binary pulses positioned over time as a function of the light variations in the scene for the pixel. Alternatively, the information representing the event may comprise a first pulse positioned over time as a function of the light variations in the scene for the pixel, and a second pulse positioned over time as a function of a greyscale for the display of the pixel.

In one embodiment of the proposed method, corresponding to a scenario wherein an asynchronous signal carries the information representing a plurality of events concerning the pixel, the proposed method may further comprise: detecting in the asynchronous signal information representing a second event for the pixel, and, when the time lag between the first and second events is less than a threshold, not generating a control signal for the asynchronous display of the pixel on detection of the information representing the second event. The threshold, which may be predetermined, may be chosen between 1 ms and 40 ms, and for example set to a value of the order of 30 ms.

According to a further aspect, the invention proposes a device for controlling the display of images in the form of a pixel array, comprising an input interface configured to receive asynchronous information representing events for at least one pixel of the array, and a pixel activation control unit, coupled operationally with the input interface, and configured to actuate the activation of the pixel according to the various embodiments of the proposed method.

In one embodiment of the proposed device, the events in question correspond respectively to light variations in a scene for the pixel.

In one embodiment, the device further comprises an output interface, coupled operationally with the pixel activation control unit, to deliver pixel activation commands.

According to a further aspect, the invention proposes an image display, comprising a display unit providing a pixel array, and a device for controlling the display of images in the form of a pixel array according to the various proposed embodiments to control the display unit.

According to a further aspect, the invention proposes a computer program, loadable in a memory associated with a processor, and comprising portions of code for implementing the steps of the proposed method during the execution of said program by the processor, along with a set of data representing, for example by compression or encoding means, said computer program.

BRIEF DESCRIPTION OF THE DRAWINGS

Further specificities and advantages of the present invention will emerge in the description hereinafter of non-limiting examples of embodiments, with reference to the appended figures, wherein.

DETAILED DESCRIPTION OF THE PREFERRED EMBODIMENTS

In the detailed description hereinafter of embodiments of the invention, numerous specific details are given to provide more comprehensive understanding. Nevertheless, those skilled in the art can be aware that embodiments may be put into practice without these specific details. In other cases, well-known features are not described in detail to avoid complicating the description unnecessarily.

The invention will be described hereinafter in the non-limiting context of asynchronous information representing, for a pixel of a pixel array, events corresponding to light variations concerning the pixel. The methods and devices proposed are however not limited to this particular embodiment, the events relating to the pixel may according to the embodiment correspond to light variations concerning the pixel, the detection of a shape of interest or the detection of a primitive, and more generally to any type of asynchronous information concerning the pixel.

Figure 1:
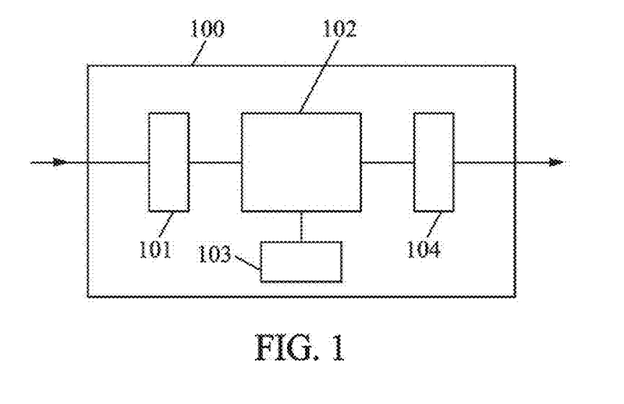
FIG. 1 is a synoptic diagram of a control display device suitable for implementing the proposed method according to one embodiment.

FIG. 1 shows a display control system 100 comprising an input interface 101 for receiving asynchronous information, a data processing unit 102, memory means 103, and an output interface 104 for transmitting display control signals.

In one embodiment of the proposed method, the asynchronous information received on the input interface 101 represents events corresponding respectively to light variations in a scene concerning a pixel. As such, it corresponds to a sequence of images, each considered in the form of a pixel array, a pixel being an elementary object of an image. The asynchronous information received on the interface 101 may also represent events corresponding respectively to light variations relating to the image sequence for a set of pixels of the array, or for all the pixels of the array.

This information may be generated by various means. For example, it may be carried by an asynchronous signal produced by an asynchronous vision sensor and received on the input interface 101. It may also result from the encoding of a sequence of synthesised images producing a set of data received on the interface 101.

Moreover, the proposed method is not limited to a particular asynchronous information format. As a general rule, the asynchronous information represents events relating to the pixels of the array. In one particular embodiment, the asynchronous information indicates, or signals, events relating to one or a plurality of pixels. It may for example be contained in data identifying events with the respective characteristics thereof.

Hereinafter, the non-limiting scope of asynchronous information carried by a signal received on the interface 101 in optionally encoded form for the transmission and/or storage thereof is considered.

In this embodiment, the asynchronous signal received on the input interface 101 carries information representing time events corresponding to light variations in a scene. In this scenario, the input interface 101 may be configured to receive a signal produced by an event-based asynchronous image capture subsystem. This subsystem typically incorporates an event-based asynchronous vision sensor.

Figure 2A:
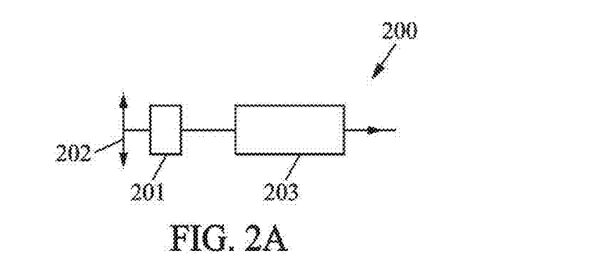
FIG. 2a is a synoptic diagram of an acquisition device suitable for generating an asynchronous signal suitable for implementing the proposed method.

FIG. 2a shows a light acquisition device 200 comprising an event-based asynchronous vision sensor 201 placed facing a scene and receiving the luminous flux from the scene via an acquisition lens 202. The sensor 201 may comprise a group of photosensitive elements organised into a pixel array, such that each pixel of the array corresponds to a photosensitive element of the sensor. For each pixel of the array, the device 200 generates an event-based asynchronous signal sequence based on light variations experienced by the pixel in the scene appearing in the field of vision of the device 200. Each pixel corresponding to a photosensitive element thus produces time events corresponding respectively to light variations in the scene.

The sensor 201 thus does not produce video frames consisting of the pixel array corresponding to the photosensitive elements of the sensors at a predetermined sampling frequency. It reacts for each pixel of the array to events corresponding to light variations concerning the pixel. Conversely, it does not produce information concerning a pixel if no event has occurred concerning this pixel. In particular, it does not perform systematic capture of luminous intensity of the pixels of the array. As such, the events to which it reacts are asynchronous, and are not dependent on a video frame acquisition frequency. This makes it possible to considerably reduce, if not suppress, the redundancies created by the acquisition of video frames at a defined rate not accounting for the lack of change of the information carried by a pixel from one frame to another.

A computer 203 processes the information from the sensor 201 and representing events produced asynchronously by the various pixels, to generate an asynchronous signal carrying this information.

Figure 2B:
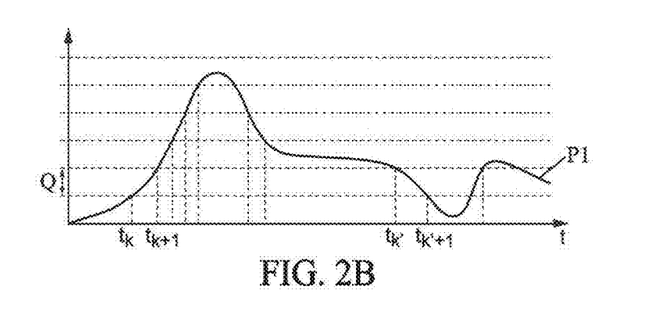
FIG. 2b is a diagram showing an example of a luminous intensity profile at the level of a pixel of an asynchronous sensor.
Figure 2C:
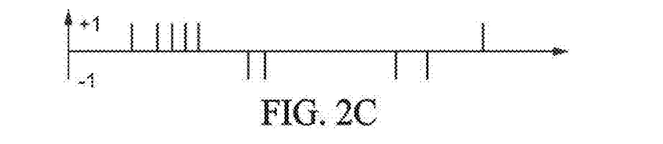
FIG. 2c shows an example of a signal delivered by the asynchronous sensor in response to the intensity profile of FIG. 2b.
Figure 2D:
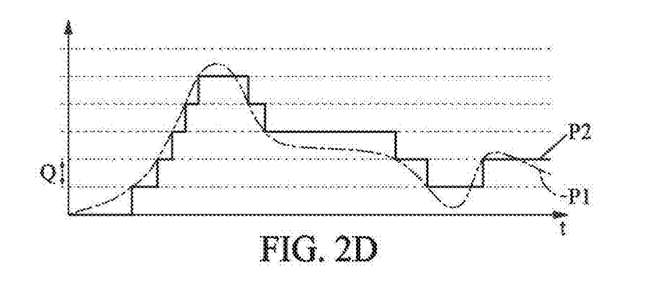
FIG. 2d illustrates the reconstruction of the intensity profile on the basis of the signal in FIG. 2c.

An example of acquisition principle using this asynchronous sensor is illustrated by FIGS. 2b-2d. According to this example, the information consists of a sequence of times, referenced $t_k$ (k=0, 1, 2, . . . ) at which an activation threshold Q is attained. The sensor 201 is thus equipped with a detector of variations which, for each pixel, measures and records the luminous intensity of the pixel when this intensity has varied beyond a threshold Q.

FIG. 2b shows an example of a luminous intensity profile P1 from the viewpoint of a pixel of the array of the asynchronous vision sensor. Whenever this intensity increases from a quantity equal to the activation threshold Q in comparison to that at the time $t_k$, a new event is identified and a positive band (level +1 in FIG. 2c) is emitted corresponding to the overshoot time of the differential threshold Q, referenced $t_{k+1}$. Symmetrically, whenever the intensity of the pixel decreases from the quantity Q in comparison to that at the time $t_{k'}$, a new event is identified and a negative band (level −1 in FIG. 2c) is emitted corresponding to the overshoot time of the differential threshold Q, referenced $t_{k'+1}$.

The asynchronous signal concerning the pixel then consists of a sequence of pulses of bands, positive or negative, positioned over time at the times $t_k$ depending on the luminous profile concerning the pixel. These bands may be represented mathematically by positive or negative Dirac peaks and each characterised by an emission time $t_k$ and a sign bit. The output of the sensor 201 is thus in the form of an address-event representation AER. The information produced by the sensor, corresponding to an event concerning a pixel, comprises a first item of information relating to an occurrence time of the event, and a second item of information relating to a luminous characteristic concerning the pixel at this time.

FIG. 2d shows the intensity profile P2 which can be reconstructed as an approximation of the profile P1 by integration over time of the asynchronous signal in FIG. 2c.

Figure 3A:
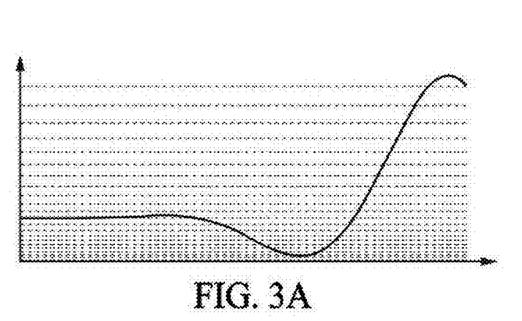
FIGS. 3a and 3b are diagrams equivalent to those in FIGS. 2b and 2c illustrating a further light acquisition mode by an asynchronous sensor.
Figure 3B:
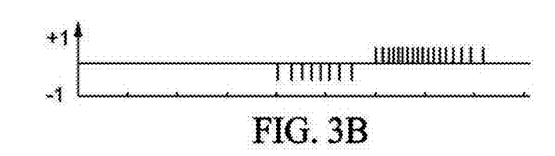

The activation threshold Q may be fixed, as in the case of FIGS. 2b-d, or adaptive according to the luminous intensity, as in the case of FIGS. 3a-b. For example, the threshold ±Q may be compared to the variations of the logarithm of the luminous intensity for the generation of an event ±1. The choice of the logarithmic scale for the measurement of the luminous intensity thus offers two advantages: firstly, it is better suited to the physiology of the eye due to the fact that the sensitivity of the retina to light is logarithmic, as described above, the threshold defined in the logarithmic scale may be adaptive.

By way of example, the sensor 201 may be of the type described in "A 128×128 120 dB 15 μs Latency Asynchronous Temporal Contrast Vision Sensor", P. Lichtsteiner, et al., IEEE Journal of Solid-State Circuits, Vol. 43, No. 2, February 2008, pp. 566-576, or in the patent application US 2008/0135731 A1, which describe a first generation of asynchronous sensors, usually referred to using the acronym DVS, for "Dynamic Vision Sensor".

The dynamic range of the retina (minimum period between the action potentials) of the order of a few milliseconds may be suitably reproduced with a sensor of this type. The dynamic performance is in any case largely greater than that which can be achieved with a conventional video camera having a realistic sampling frequency. For example, a sensor of this type makes it possible to achieve temporal resolutions of the order of one microsecond with a luminance range greater than 120 dB, which is considerably greater than CMOS/CCD standard which typically has a luminance range of 60-70 dB.

It should be noted that the form of the asynchronous signal delivered concerning a pixel by the sensor 201, which constitutes the input signal of the computer 203, may be different from a sequence of Dirac peaks, the events represented liable to have any temporal width or amplitude or waveform in this event-based asynchronous signal.

Each pixel of the position sensor p=(x; y) thus delivers a sequence of binary pulses, which can be modelled by ON or OFF events generated asynchronously at respective times $t_k$. The computer 203 is configured to generate an asynchronous signal carrying the set of events for one or a plurality of pixels of the array. The information corresponding to an event comprises position information of the pixel for which the event occurred (for example the pair (x; y) of the row and column numbers in the pixel array), information on the occurrence time of the event (for example a discrete time value with respect to a reference), and event type information (for example a bit to encode events of two types).

With reference to FIG. 1, the asynchronous signal received as an input of the interface 101 may thus carry the information representing a stream of events, each defined by a quadruplet e(x; y; t; ON/OFF) giving the position p=(x; y) of the pixel with which the event is associated, the time t at which the event was detected, and the event type (ON or OFF).

In a further particular embodiment, the asynchronous signal received as an input of the interface 101 carries information representing a stream of events, where each event is defined by a quadruplet e(x; y; t; ON/OFF) giving the position p=(x; y) of the pixel with which the event is associated, the time t at which the event was detected, and a greyscale g associated with the event.

The article by Posch, C., Matolin, D., and Wohlgenannt, R. (2011) entitled "A qvga 143 db dynamic range frame-free pwm image sensor with lossless pixel-level video compression and time-domain cds", and published in the IEEE Journal of Solid-State Circuits, 46, pages 259-275. doi: 10.1109/JSSC.2010.2085952, provides a description of examples of events encoded by greyscales.

The asynchronous information for each pixel consists here again of a sequence of pulses or bands positioned over time at the times $t_k$ depending on the luminous profile for the pixel. Each event may for example correspond to two successive pulses, the first indicating the time of the event and the second suitable for determining a greyscale for the pixel according to the time lag between the two pulses. The information corresponding to an event concerning a pixel thus comprises a first item of information relating to an occurrence time of the event, and a second item of information relating to a luminous characteristic (greyscale) concerning the pixel at this time.

This new generation of sensors capable of generating a greyscale for each event is sometimes referred to under the acronym ATIS, for "Asynchronous, Time-Based Image Sensor". The capture sub-system and the ATIS sensor incorporated therein may be for example of the type described in the article by C. Posch et al., entitled "An Asynchronous Time-based Image Sensor" (IEEE International Symposium on Circuits and Systems, pages 2130-2133), or of the type described in the article by C. Posch et al., entitled "A QVGA 143 db dynamic range frame-free pwm image sensor with lossless pixel-level video compression and time-domain CDS" (46(1):259275, 2011).

With reference to FIG. 1, the data processing unit 102 may be a computer, a computer network, or another device comprising a processor, optionally coupled operationally with a memory 103, and suitable for further including a data storage unit, and further hardware components such as a network interface and a medium reader to read a removable storage medium and write on such a medium (not represented in the figure). The removable storage medium may be, for example, a compact disc (CD), a digital versatile/video disc (DVD), a flash drive, a USB key, etc. According to the embodiment, the memory 103, the data storage unit or the removable storage medium contains instructions which, when executed by the data processing unit 102, lead this unit 102 to perform or control the input 101 and/or output 104 interface and/or data processing parts of the examples of implementation of the proposed method described herein. The processing unit 102 may be a component implementing a processor or a computing unit for the generation of display commands according to the proposed method and the control of the input 101 and output 104 interfaces of the system 100.

Moreover, the display control system 100 may be embodied in software form, as described above, or in hardware form, as an application-specific integrated circuit (ASIC), or in the form of a combination of hardware and software elements, such as for example a software program intended to be loaded and executed on a FPGA (Field Programmable Gate Array) type component.

The control system 100 generates display commands wherein the format is adapted to the display system to which these commands are transmitted via the output interface 104. The proposed method is applicable to the control of all types of display system, such as screen display systems, projection systems, or vision aid devices.

The output interface 104 may thus comprise a driver module (not represented in FIG. 1) suitable for adapting the output signals of the system 100 to the input interface of the display system.

For example, in the case where the display system is a prosthesis fitted on the retina, the driver module of the interface 104 will convert the control signals to analogue electrical potentials which will be transmitted via the interface 104 to the electrodes of the prosthesis.

In one particular embodiment of the proposed method, the output interface 104 is configured to generate an output signal of suitable formation for controlling a video projector using micromirror array technology (DMD for "Digital Micromirror Device"). This type of projector is sometimes referred to as the acronym DLP, for "Digital Light Processing", and functions with a light source which illuminates a micromirror array which vibrate according to the amount of light to be reflected. The vibrations of each mirror are performed about two positions corresponding respectively to angles of inclination about an axis, one wherein the light is reflected by the mirror to an output lens, and the other wherein the light is reflected by the mirror to an absorbent surface and is thus not projected. Each mirror of the DMD array projects light concerning a pixel to a display screen.

Some DLP projectors are further capable of illuminating pixels with different greyscales, and can thus receive display commands concerning each pixel comprising information relating to a greyscale with which the pixel is to be displayed. It will be possible for example to use a DLP projector capable of handling 1024 greyscales, and supply same with display commands according to the proposed method wherein the illumination greyscale of a pixel is encoded on 10 bits.

The DLP projector controlled using the proposed method may for example be of the type mounted on "DLP Lightcrafter" evaluation platforms. This type of device may for example comprise a DMD component 4.6 mm×5.2 mm in size, and support a display resolution, i.e. a displayed image size in pixels, of 608×684 pixels (corresponding to the WVGA standard) and a temporal resolution of up to 1440 Hz.

As such, in the case where the display system is a DLP projector, the driver module of the interface 104 converts the control signals to interface the display control system 100 with an input of the DLP projector.

Figure 4A:
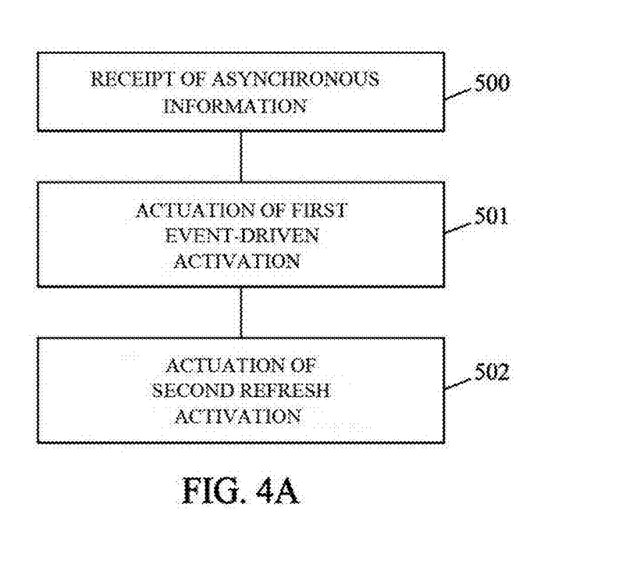
FIGS. 4a and 4b are diagrams illustrating embodiments of the proposed method.

With reference to FIGS. 1 and 4a, the display control device 100 independently controls each pixel of a pixel array for the activation of said pixel. The device 100 receives (500) via the input interface 101 asynchronous information representing events corresponding to light variations concerning the pixel.

For example, for a pixel of position $(x_o, y_o)$ in the pixel array (pixel positioned on the row of index $x_o$ and on the column of index $y_o$ in an array M×N, where $x \in \{0, \ldots, M-1\}$ and $y \in \{0, \ldots, N-1\}$, the information received will comprise asynchronous information concerning the pixel of position $(x_o, y_o)$.

The asynchronous information is processed by the data processing unit 102 in order to identify an event concerning the pixel in order to actuate (501) a first activation of the pixel at an activation time determined by the event identified.

In one particular embodiment, the identification of an event may relate to events characterised by a first item of information indicating a time of occurrence of the event, and a second item of information relating to a luminous characteristic concerning the pixel at a corresponding time. For example, the identification of an event may comprise the detection of two peaks or pulses in a signal carrying the asynchronous information, the first indicating a time of occurrence of the event and the second a characteristic greyscale of the event concerning the pixel.

In the embodiment wherein the events are characterised by the time of occurrence of a variation of luminous intensity beyond a threshold and the direction of this variation, the activation command may comprise an illumination level of the pixel determined by accounting for the detected variation applied to the illumination level of the preceding display command of the pixel.

In the embodiment wherein the events are characterised by the time of occurrence of a variation of luminous intensity beyond a threshold and a greyscale associated with this variation, the activation command may comprise an illumination level of the pixel corresponding to the greyscale determined following the detection of the event.

This first activation of the pixel is thus actuated on identifying an event concerning a pixel using the asynchronous information received at the input of the display control system 100. In one particular embodiment, the activation is controlled once an event is identified concerning a pixel, by means of the processing time required for the system 100 for processing event-related information. Alternatively, the system 100 may maintain an activation time reference, on the basis whereof the pixel activations will be actuated at times corresponding to the events identified concerning each pixel. As described above, each event may be characterised by a time of occurrence and one or a plurality of values corresponding to respective luminous information (luminous intensity, greyscale, colour, etc.).

A second activation of the pixel is actuated (502) following the first activation in order to repeat same at respective times defined by a refresh sequence. The first activation is thus followed by one or a plurality of activations intended to refresh the activation actuation on identification of an event.

In one particular embodiment of the proposed method, the refresh sequence defines activation times of the pixel separated by a time interval. This time interval may be common to the set of pixels of the array or well defined for each pixel or for various pixel subsets. It may notably be determined according to the retinal persistence of the human eye. This makes it possible to choose sufficiently large refresh interval values to prevent the display of redundant information at a high frequency at the expense of the efficiency of the system, while accounting for the duration of retinal persistence of the preceding display. For example, the refresh time interval may be chosen between 40 ms and 150 ms, given that the higher the value chosen, the greater the gain of the activation control system in efficiency by especially preventing redundant activations.

A second activation of the pixel is thus actuated to perform a refresh of the activation of the pixel during the time interval determined in this way and running from the activation of the pixel following the preceding activation command.

These preceding activation command may be an event identification-driven activation command as described above, or a refresh activation command in the case for example where no activation on event identification has been actuated for a time corresponding to the refresh time interval running from the preceding activation of the pixel.

Figure 4B:
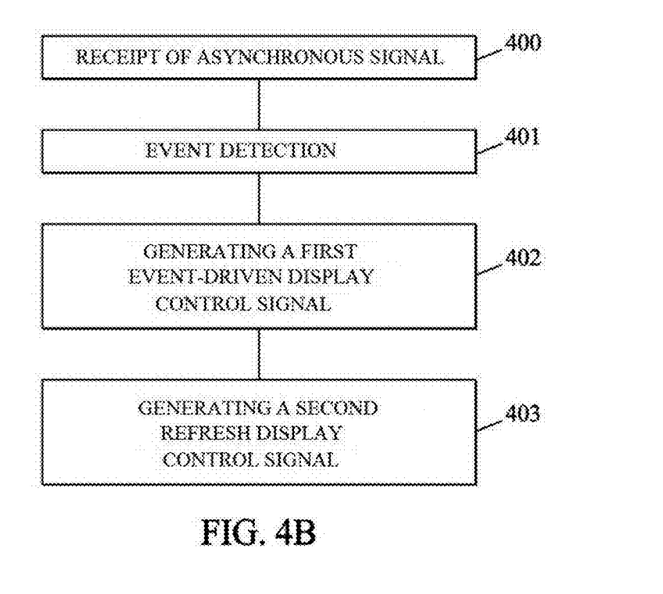

FIG. 4b illustrates a particular embodiment of the proposed method, wherein the device 100 in FIG. 1 receives a signal carrying asynchronous information, processes this signal to detect events, and then generates pixel activation commands for the illumination of the pixel, for example by projection onto a display screen.

With reference to FIGS. 1 and 4b, the display control device 100 independently controls each pixel of a pixel array for the activation of said pixel. The device 100 receives (400) via the input interface 101 asynchronous information representing events corresponding to light variations concerning the pixel.

For example, for a pixel of position $(x_o, y_o)$ in the pixel array (pixel positioned on the row of index $x_o$ and on the column of index $y_o$ in an array M×N, where $x \in \{0, \ldots, M-1\}$ and $y \in \{0, \ldots, N-1\}$, the asynchronous signal received will comprise a signal sequence concerning the pixel of position $(x_o, y_o)$.

The asynchronous signal is processed by the data processing unit 102 in order to detect (401) information representing an event concerning the pixel.

In one embodiment, the detection of information representing an event may relate to events characterised by the time of occurrence of a variation of luminous intensity beyond a threshold (which may be, in one embodiment, specific to the pixel) and the direction of this variation. For example, the detection may comprise the detection of a pulse wherein the positioning with respect to a time reference corresponds to the time of occurrence of a variation of luminous intensity beyond a threshold and wherein the type (for example ON or OFF, or +1 or −1) will correspond to the direction of luminous variation.

In a further embodiment of the proposed method, the detection of information representing an event may relate to events characterised by the time of occurrence of a variation of luminous intensity beyond a threshold (which may be, in one embodiment, specific to the pixel) and a greyscale associated with this variation. For example, the detection may comprise the detection of a first pulse wherein the positioning with respect to a time reference corresponds to the time of occurrence of a variation of luminous intensity beyond a threshold and the detection of a second pulse wherein the time lag with the first pulse will make it possible to infer a greyscale for the pixel.

The information representing an event concerning the pixel is processed by the data processing unit 102 in order to generate (402) a first pixel display control signal.

The asynchronous nature of the input signal of the display control device 100 will be especially observed because the generation and transmission time of a display command of the pixel from the time when an event is detected concerning the pixel will be short. Real-time processing will thus be preferred so as to obtain a quasi-instantaneous display of the events detected concerning each pixel.

The first display command, generated on detection of an event concerning a pixel, is transmitted to the display system with which the display control system 100 is interfaced via the output interface 104.

In the embodiments using a screen display system, the screen display may be performed following the receipt of the display command with a delay corresponding to the processing time of the command and to the temporal resolution of the display system.

For example, as described above, a DLP projector may be used to receive display commands generated according to the proposed method, in a configuration where the temporal resolution thereof is close to 1440 Hz. This temporal resolution of 1440 Hz corresponds to a possibility of display every 0.69 ms. A DLP projector may thus project light corresponding to the illumination of a pixel of an image no later than 0.69 ms after having received and processed a display command generated according to the proposed method.

This first pixel display, performed on detection of an event concerning the display, is followed by a second display intended to refresh the preceding event detection-driven display. This second display gives rise to the generation (403) of a second display command. This second display command is generated such that the display resulting therefrom enables the refresh of the display previously performed for the pixel. For this purpose, a refresh time interval is determined, wherein the duration defines the maximum time lag between two displays concerning a pixel.

This time interval may be common to the set of pixels of the array or clearly defined for each pixel or for various pixel subsets.

In one particular embodiment of the method, it is determined according to the retinal persistence of the human eye. This makes it possible to choose sufficiently large refresh interval values to prevent the display of redundant information at a high frequency at the expense of the efficiency of the system, while accounting for the duration of retinal persistence of the preceding display.

For example, the refresh time interval may be chosen between 40 ms and 150 ms, given that the higher the value chosen, the greater the gain of the activation control system in efficiency by especially preventing redundant activations.

A second display control signal is thus generated (403) to perform a refresh of the activation of the pixel during the time interval determined in this way and running from the activation of the pixel following the preceding activation command.

This preceding display command may be an event detection-driven display command as described above, or a refresh display command in the case for example where no event detection-driven display command has been generated for a time corresponding to the refresh time interval running from the preceding display.

Figure 5A:
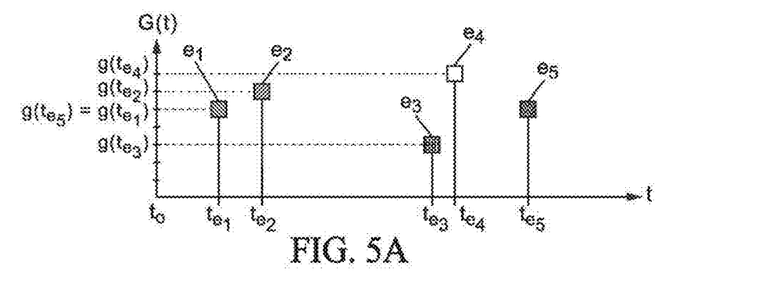
FIGS. 5a and 5b are diagrams showing a time sequence of events received in an asynchronous signal for implementing the proposed method.
Figure 5B:
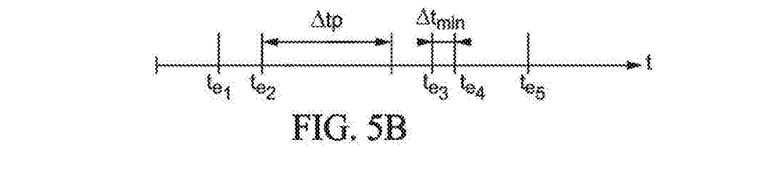

FIGS. 5a and 5b illustrate an asynchronous signal sequence concerning a pixel and the corresponding display commands generated according to one embodiment of the proposed method.

FIG. 5a illustrates the information carried by an asynchronous signal sample wherein the events concerning a pixel are represented on a time axis by Dirac peaks of amplitude G(t) corresponding to a greyscale. Five events $e_1$, $e_2$, $e_3$, $e_4$ and $e_5$ are represented in FIG. 5a, positioned respectively at the times te1, te2, te3, te4 and te5 with respect to a time reference t0, where $te_1<te_2<te_3<te_4<te_5$. Each of the 5 events carries greyscale information concerning the pixel in question annotated $g(t=te_i)$, where i={1, 2, 3, 4, 5}.

These greyscale values may for example result from the quantification of a greyscale value on $2^{n_{quant}}$ levels and encoded on $n_{quant}$ bits.

FIG. 5b shows a simplified view of the event sequence illustrated by FIG. 5a illustrated by FIG. 5a wherein the events are represented by Dirac peaks of constant amplitude. The time interval $\Delta t_p$ is defined as a function of the retinal persistence of the eye and so as to correspond to a maximum time interval separating two consecutive displays of the same pixel. In the example illustrated in FIG. 5b, the time lags separating two consecutive displays do not exceed the quantity $\Delta t_p$, with the exception of the lag between the events $e_2$ and $e_3$, $te_3$-$te_2$.

In the example of a sequence of events illustrated in FIGS. 5a and 5b, a display command of the pixel may be generated following the detection of the event $e_1$ for a display with the characteristics (typically a greyscale) carried by the asynchronous signal processed for the event $e_1$. The same applies for the events $e_2$, $e_3$, $e_4$ and $e_5$, the detections whereof, in one embodiment, may each give rise to the generation of a display command with respective characteristics.

In one particular embodiment of the proposed method, a display command will further be generated to perform a refresh display in a time interval following the display of the pixel on detection of the event $e_2$. This display command may for example be generated if no event has been detected in the time interval $[te_2; te_2+\Delta t_p]$ of duration $\Delta t_p$ from the time $te_2$.

Alternatively, it may be generated at any time throughout the time interval $[te_2; te_2+\Delta t_p]$ of duration $\Delta t_p$ from the time $te_2$.

Figure 5C:
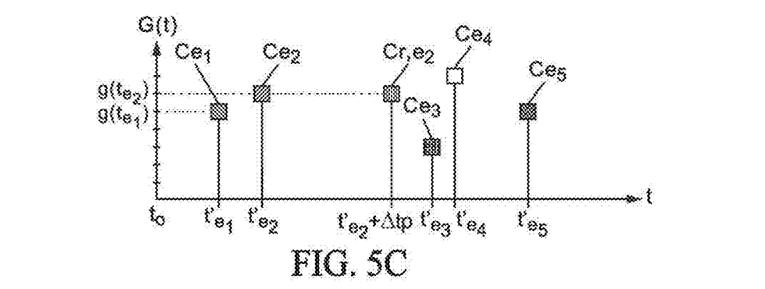
FIGS. 5c and 5d are diagrams showing a time sequence of display commands generated according to particular embodiments of the proposed method.

FIG. 5c shows an example of a sequence of display commands generated according to one embodiment of the proposed method applied to the sequence of events in FIG. 5a. The display commands are represented in the figure by Dirac peaks of variable amplitude. It shows display commands $Ce_1$, $Ce_2$, $Ce_3$, $Ce_4$ and $Ce_5$ corresponding respectively to the events $e_1$, $e_2$, $e_3$, $e_4$ and $e_5$ in FIG. 5a generated respectively at times $tce_1$, $tce_2$, $tce_3$, $tce_4$ and $tce_5$. Each of the commands comprises information relating to the greyscale at which the pixel is to be illuminated, referenced in the figure $g(te_i)$, where $i=\{1, 2, 3, 4, 5\}$.

Besides the display commands $Ce_i$ generated on detection of an event $e_i$, a refresh display command $Cr,e_2$ is generated at the time $t'e_2+\Delta t_p$ following the non-detection of a new event following that of the event $e_2$ for a time $\Delta t_p$.

The refresh display command $Cr,e_2$ may be generated with the same display characteristics, and for example the same greyscale $g(te_2)$, as those comprised in the event-driven display command $Ce_2$. Alternatively, the refresh display command $Cr,e_2$ may be generated with display characteristics determined as a function of those determined for the event-driven display command $Ce_2$.

In one particular embodiment of the proposed method, the management of the refresh time interval concerning each pixel may be carried out using a delay counter, set to the value $\Delta t_p$ defined for the pixel and triggered on each generation of a display command concerning the pixel. Alternatively, a refresh delay counter may be engaged for a pixel following each transmission of a display control signal for the pixel. This delay counter may be stopped on detection of a new event for which the display control system determines that a display command is to be generated, and on expiration when no display command has been generated during the interval $\Delta t_p$ which will give rise to the generation of a refresh display command concerning the pixel.

Alternatively, the pixels of the array may be refreshed as a group, and a systematic and periodic refresh of the pixels of the array may be performed at a predetermined refresh frequency. The advantage of this embodiment is that of avoiding individualised management of each pixel in respect of refreshing. The refresh of the array is then repeated at a rate at least equal to the shorter refresh interval defined for a pixel.

In this embodiment of the proposed method, the pixel array is refreshed periodically, while remaining completely decorrelated and independent of the event-driven display command sequence. The generation of the display refresh command is independent of that of the event-driven display command, and the display refresh frequency is chosen such that the lag between an event-driven display of each pixel and the immediately subsequent refresh display does not exceed a time interval $\Delta t_p$ which, as discussed above, may be chosen as a function of the retinal persistence of the human eye of the order of 40 ms to 150 ms. This "combined" display mode makes it possible to combine an event-driven display operating asynchronously with a periodic refresh period performed synchronously. As such, according to the occurrence of the events concerning each pixel, the refresh display of the pixel may occur within a very short time interval following an event-driven display of the pixel, or following a time following an event-driven display of the pixel defined as the maximum interval between two displays of the pixel. This combined mode makes it possible to simplify the management of the refresh of the display, while limiting by means of the asynchronous event-driven display concerning each pixel the display of the redundant information, given that the asynchronous display makes it possible to choose low refresh frequencies in comparison to current systems.

With reference to FIG. 1, each event-driven display command generation may for example give rise to the storage in memory 103 by the data processing unit 102 of display characteristics relating to the command generated, such that these characteristics may be retrieved by the unit 102 for the management of the refresh display.

Figure 5D:
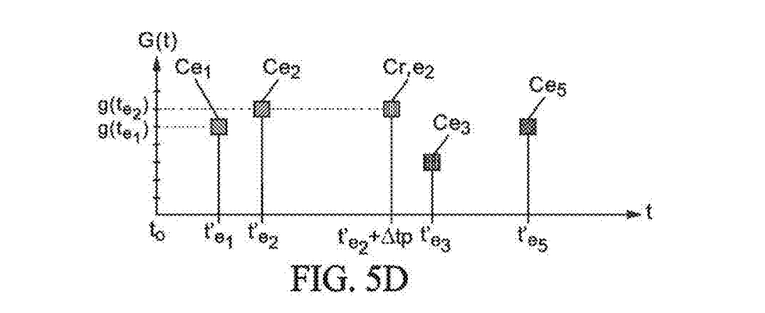

FIG. 5d represents schematically a sequence of display commands generated according to a further embodiment of the proposed method applied to the event sequence in FIGS. 5a and 5b.

With reference to FIG. 5b, the event e4 is detected with a time lag $te_4-te_3$ lower than the time interval $\Delta_{tmin}$ defined as the minimum time interval separating two successive event-driven display commands of the pixel.

The sequence of display commands in FIG. 5d differs from the sequence illustrated by FIG. 5c in that no display command is generated for the event $e_4$, given than the time lag between the time of detection of this event and the time of detection of the immediately preceding event is less than a predefined threshold $\Delta_{tmin}$.

In one particular embodiment of the proposed method, the management of the separation time interval concerning each pixel may be carried out using a delay counter, set to the value $\Delta_{tmin}$ defined for the pixel and triggered on each generation of an event-driven display command concerning the pixel. For example, an event detected while this delay counter has not expired for the pixel may lead to the event being ignored and not generating a corresponding event-driven display command.

The display characteristics carried by the asynchronous information for this ignored event may also be ignored. Alternatively, it is possible to envisage an embodiment whereby, even when no event-driven display command is generated, the display characteristics corresponding to the event are recorded in memory 103 to be used subsequently, for example for the next refresh display of the pixel.

According to one embodiment, a single delay counter may be used for the management of the refresh interval and that of the separation interval. This delay counter may be triggered on each generation of a display command for the pixel, by recording an indicator in memory suitable for distinguishing between event-driven display commands and refresh display commands.

Figure 6:
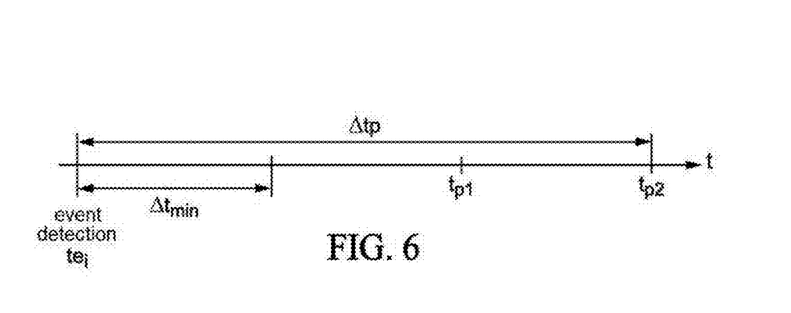
FIG. 6 is a diagram illustrating time intervals taken into account in the embodiments of the proposed method.

FIG. 6 illustrates various periods of the management of the display of a pixel according to one embodiment of the proposed method, indicated on a time axis.

The detection of an event $e_i$ from which an event-driven display command is generated constitutes the starting point referenced $te_i$ of a so-called refractory period, during which it is not considered useful to display a new event. This period has a duration referenced $\Delta_{tmin}$ which corresponds to the separation interval described above, and may be chosen within an interval ranging from 1 ms to 40 ms, and set for example to a value of the order of 30 ms. The value of this period may be chosen according to the computing limitations of the system implementing the proposed method and/or the degree of precision sought. It may further be defined dynamically by the type of movements potentially present in the scene.

Beyond this period $\Delta_{tmin}$, it is preferably to display a new event detected for the pixel. Two times referenced respectively $tp_1$ and $tp_2$ define a time interval during which it is preferable to perform the refresh display of the pixel. The time lag between $te_1$ and $te_e$ corresponds to the refresh interval, referenced $\Delta t_p$, described above. The system is configured to generate a refresh display of the last event-driven display of the pixel during the time interval $\Delta t_p$. Alternatively, the starting point $te_i$ of the interval $\Delta t_p$, may for example correspond to the generation of the event-driven display command, or also to the transmission of the command once generated.

The threshold determined by $tp_1$ may be used to avoid performing a refresh display of the pixel which is too close to the initial event-driven display.

According to one embodiment, an event $e_{i+1}$ following the event ei detected as occurring after the refractory period of duration $\Delta_{tmin}$, gives rise to the generation of a display command. The delay counter(s) in respect of the management of the refractory period and management of the refresh display, respectively, are reset from the time $te_{i+1}$, which may correspond to the time of detection of the event $e_{i+1}$, to the time of generation of the corresponding command or the transmission thereof.

On the other hand, if no event $e_{i+1}$ following the event $e_i$ is detected at the time $tp_1$, a refresh display command is generated in the time interval $[tp_1, tp_2]$, for example at the time $tp_1$, or at any time between $tp_1$ and $tp_2$, including $tp_2$, if at this time no event $e_{i+1}$, following the event $e_i$ has been detected yet.

The synchronous and asynchronous modes may be compared by examining the rate of refreshed pixels at a given period. For example, a display of the conventional type (referred to as "synchronous") on a screen with a refresh frequency of 200 Hz will give rise to a display of a given pixel every 5 ms. An asynchronous type display may be performed with a minimum time lag of 5 ms and a maximum time lag of 40 ms, only the pixels corresponding to a motion zone in the displayed image sequence being displayed every 5 ms, the refresh displays only occurring for example every 40 ms for the pixels not corresponding to a motion zone.

In order to determine the gain in terms of non-refreshed pixels of the asynchronous display mode, a number of pixels belonging to moving zones may be determined, and the percentage of non-refreshed pixels at 200 Hz in asynchronous mode calculated with respect to synchronous mode over a period of one second.

Figure 7:
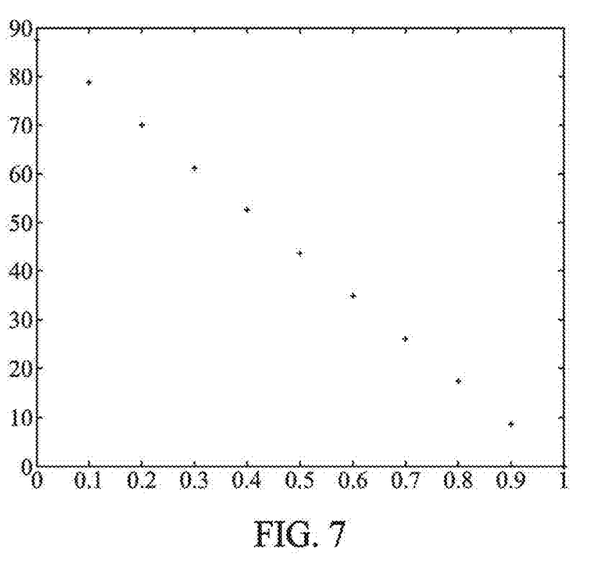
FIG. 7 illustrates the variation of the number of non-refreshed pixels in asynchronous display (or activation) mode with respect to an asynchronous display (or activation) according to the number of pixels contained in the motion zones of an image sequence.

FIG. 7 shows the variation of the number of non-refreshed pixels in asynchronous mode with respect to a synchronous display as a function of the number of pixels contained in the motion zones. The quantities are expressed in percentages, and the graph in FIG. 7 shows the percentage of non-refreshed pixels (y-axis) in asynchronous mode with respect to a synchronous mode for a 200 Hz display as a function of the percentage of pixels belonging to a motion zone (x-axis).

Though described via a number of detailed examples of embodiments, the display control method and the equipment for implementing the method comprises various alternative embodiments, modifications and improvements which will seem obvious to those skilled in the art, it being understood that these embodiments, modifications and improvements are part of the scope of the invention, as defined by the claims hereinafter.

For example, in one embodiment, the proposed method is a method for controlling the display of animated images in the form of a pixel array, comprising: receiving the asynchronous information indicating, for each pixel of the array, successive events dependent on light variations in a scene; activating the pixels of the array at respective times, each activation time of a pixel being determined by a respective event indicated by the asynchronous information concerning said pixel; after activation of a pixel of the array at a time determined by an event indicated by the asynchronous information, repeating the activation of said pixel substantially at the same level of activation at times defined by a refresh sequence until the determination of a future activation time of said pixel by events indicated by the asynchronous information.

Alternatively, the pixels of the array may be activated at respective times determined by events indicated by the asynchronous information concerning said pixels.

The invention further proposes a corresponding device for controlling the display of animated images in the form of a pixel array, comprising: an input receiving the asynchronous information indicating, for each pixel of the array, successive events dependent on light variations in a scene; a unit for activating the pixels of the array, arranged to activate each pixel of the array at times determined by respective events indicated by the asynchronous information concerning said pixel; and after activation of a pixel of the array at a time determined by an event indicated by the asynchronous information, repeating the activation of said pixel substantially at the same level of activation at times defined by a refresh sequence until the determination of a future activation time of said pixel by events indicated by the asynchronous information.

Furthermore, various aspects and characteristics described above may be implemented together, or separately, or substituted with one another, and all the various combinations and sub-combinations of the aspects and characteristics are part of the scope of the invention. Moreover, it is possible that some systems and equipment described above do not incorporate all the modules and functions described for the preferred embodiments.

The information and signals defined in the present document may be represented according to a multitude of technologies and techniques. For example, instructions, messages, data, commands, information, signals, bits and symbols may be represented by voltages, intensities, electromagnetic waves or a combination thereof.

According to the embodiment chosen, some procedures, actions, events or functions of each of the methods described in the present document may be performed or occur according to a different order to that wherein they have been described, or may added, merged or not be performed or not occur, according to the circumstances. Moreover, in some embodiments, some procedures, actions or events are performed or occur concurrently and not successively.

The invention claimed is:

1. An image display, comprising:
a display unit providing a pixel array; and
a controlling device for controlling the display of images as a pixel array, the controlling device including:
an input interface configured to receive, from an asynchronous event-based vision sensor, asynchronous information representing events for at least one pixel of the image, each event among the events corresponding to a variation of light concerning said pixel beyond a threshold, and
a pixel activation control unit, coupled operationally with the input interface, and configured to
actuate a first activation of the pixel at an activation time determined by a first event of the asynchronous information, and
actuate at least a second activation of the pixel in order to repeat the first activation of the pixel at respective times defined by a refresh sequence.

2. A control device for controlling the display of images as a pixel array, comprising:
an input interface configured to receive, from an asynchronous event-based vision sensor, asynchronous information representing events for at least one pixel of the image, each event among the events corresponding to a variation of light concerning said pixel beyond a threshold; and a pixel activation control unit, coupled operationally with the input interface, and configured to:

actuate a first activation of the pixel at an activation time determined by a first event of the asynchronous information, and actuate at least a second activation of the pixel in order to repeat the first activation of the pixel at respective times defined by a refresh sequence.

3. The control device according to claim 2, further comprising:

an output interface, coupled operationally with the pixel activation control unit, to deliver pixel activation commands.

4. A non-transitory computer readable storage medium, having stored thereon a computer program comprising program instructions, the computer program being readable by a data-processing unit and adapted to cause the data-processing unit to carry out, upon execution by the data-processing unit, operations for controlling a display of images as a pixel array, said operations including, for a pixel of the array:

receiving, from an asynchronous event-based vision sensor, asynchronous information representing events concerning the pixel, each event among the events corresponding to a variation of light concerning said pixel beyond a threshold;

actuating a first activation of the pixel at an activation time determined by a first event of the asynchronous information;

actuating at least a second activation of the pixel in order to repeat the first activation of the pixel at respective times defined by a refresh sequence.

5. A method for controlling a display of images as a pixel array, the method comprising, for a pixel of the array:

receiving, from an asynchronous event-based vision sensor, asynchronous information representing events concerning the pixel, each event among said events corresponding to a variation of light concerning said pixel beyond a threshold;

actuating a first activation of the pixel at an activation time determined by a first event of the asynchronous information;

actuating at least a second activation of the pixel in order to repeat the first activation of the pixel at respective times defined by a refresh sequence.

6. The method according to claim 5, wherein the first activation actuation of the pixel is repeated according to the refresh sequence until determination of a next activation time of the pixel by events of the asynchronous information.

7. The method according to claim 5, wherein the reception of the asynchronous information comprises a reception of a signal carrying the asynchronous information, and the first activation actuation of the pixel comprises a detection in the signal of a first item of information representing the first event and the activation actuation on detection of the first item of information representing the first event.

8. The method according to claim 5, wherein the refresh sequence defines activation times of the pixel separated by a time interval.

9. The method according to claim 8, wherein the time interval is determined according to retinal persistence of human eye.

10. The method according to claim 8, wherein the time interval is greater than 40 ms and lower than 800 ms.

11. The method according to claim 5, wherein the activation actuations are delivered as electric stimulations applied to a visual prosthesis of a vision aid device.

12. The method according to claim 8, wherein the activation is refreshed substantially simultaneously for a plurality of pixels of the pixel array.

13. The method according to claim 7, wherein the signal comprises a train of binary pulses positioned over time as a function of light variations in a scene for the pixel.

14. The method according to claim 5, wherein the information representing the first event comprises a first pulse positioned over time as a function of light variations in a scene for the pixel, and a second pulse positioned over time as a function of a greyscale for the activation of the pixel.

15. The method according to claim 5, further comprising:

detecting in the asynchronous information a second item of information representing a second event for the pixel; and when a time lag between the first and second events is lower than a threshold, not actuating the activation of the pixel at an activation time determined by the second event.

16. The method according to claim 15, wherein the threshold is between 1 ms and 40 ms.

* * * * *